United States Patent
Dupps, Jr.

(10) Patent No.: US 10,141,075 B2
(45) Date of Patent: Nov. 27, 2018

(54) PREDICTING AND MITIGATING RISK OF ECTASIA AND OPTIMIZING THERAPEUTIC OUTCOMES

(71) Applicant: THE CLEVELAND CLINIC FOUNDATION, Cleveland, OH (US)

(72) Inventor: William J. Dupps, Jr., Bay Village, OH (US)

(73) Assignee: THE CLEVELAND CLINIC FOUNDATION, Cleveland, OH (US)

(*) Notice: Subject to any disclaimer, the term of this patent is extended or adjusted under 35 U.S.C. 154(b) by 60 days.

(21) Appl. No.: 15/118,999

(22) PCT Filed: Feb. 13, 2015

(86) PCT No.: PCT/US2015/015749
§ 371 (c)(1),
(2) Date: Aug. 15, 2016

(87) PCT Pub. No.: WO2015/123492
PCT Pub. Date: Aug. 20, 2015

(65) Prior Publication Data
US 2016/0364543 A1 Dec. 15, 2016

Related U.S. Application Data

(60) Provisional application No. 61/939,293, filed on Feb. 13, 2014.

(51) Int. Cl.
*G06K 9/00* (2006.01)
*G16H 50/50* (2018.01)
(Continued)

(52) U.S. Cl.
CPC ......... *G16H 50/50* (2018.01); *G06F 17/5018* (2013.01); *G06F 19/00* (2013.01); *G06T 7/0014* (2013.01); *G06T 2207/30041* (2013.01)

(58) Field of Classification Search
None
See application file for complete search history.

(56) References Cited

U.S. PATENT DOCUMENTS

2007/0260157 A1* 11/2007 Norrby ............... A61B 3/0025
600/558
2009/0271155 A1* 10/2009 Dupps, Jr. ........... G06F 19/3437
703/1

(Continued)

FOREIGN PATENT DOCUMENTS

DE 102008046834 A1 3/2010

OTHER PUBLICATIONS

PCT International Search Report and Written Opinion for corresponding PCT/US2015/015749, dated Aug. 20, 2015, pp. 1-14.

*Primary Examiner* — Hadi Akhavannik
(74) *Attorney, Agent, or Firm* — Tarolli, Sundheim, Covell & Tummino LLP

(57) ABSTRACT

Systems and methods are provided for evaluating an eye of a patient. A modeling component is configured to determine a representation of at least the cornea of the eye from a three-dimensional structural image of the eye and at least one biomechanical property of the eye. A feature extractor is configured to extract a plurality of features from the model of at least the cornea of the eye. An ectasia evaluation component is configured to calculate at least one parameter associated with the risk of ectasia in the eye from the extracted plurality of features. A system output is configured to provide the calculated at least one parameter to one of a treatment system and a user.

15 Claims, 4 Drawing Sheets

(51) Int. Cl.
*G06F 17/50* (2006.01)
*G06T 7/00* (2017.01)
*G06F 19/00* (2018.01)

(56) References Cited

U.S. PATENT DOCUMENTS

2010/0049447 A1   2/2010  Peyman et al.
2011/0242482 A1* 10/2011  Olsen .................. A61B 3/0025
                                               351/205
2013/0237970 A1*  9/2013  Summers ............ A61F 9/00827
                                               606/5

* cited by examiner

PREDICTING AND MITIGATING RISK OF ECTASIA AND OPTIMIZING THERAPEUTIC OUTCOMES

RELATED APPLICATIONS

This application claims priority from U.S. Provisional Application No. 61/939,293, filed Feb. 13, 2014, the subject matter of which is incorporated herein by reference.

GOVERNMENT FUNDING

This invention was made with government support under EY023381 awarded by the National Institutes of Health. The government has certain rights in the invention.

FIELD OF THE INVENTION

The present invention relates to systems and methods for evaluating the condition and properties of a mammalian eye, and, in particular, is directed to systems and methods for predicting and mitigating ectasia risk and optimizing therapeutic outcomes.

BACKGROUND OF THE INVENTION

The cornea relies greatly upon its material properties in its roles as a mechanical barrier to injury and as a scaffold for the eye's primary refracting surface. These biomechanical properties influence the safety and optical predictability of surgery and play an important role in the pathogenesis and of diseases such as keratoconus and post-refractive surgery ectasia. Consequently, alteration of these properties by disease or surgery can have profound visual implications. Ectatic diseases such as keratoconus, pellucid marginal degeneration and keratoglobus are characterized by progressive thinning and distortion of the cornea, and as a class represent a leading indication for corneal transplantation. Identification of early ectasia or predisposition to ectasia is a major emphasis of preoperative refractive surgery evaluations, where it is imperative to avoid the potential destabilizing effects of laser vision correction in corneas that are predisposed to biomechanical instability or failure.

SUMMARY OF THE INVENTION

In accordance with an aspect of the present invention, a system is provided for evaluating an eye of a patient. A modeling component is configured to determine a representation of at least the cornea of the eye from a three-dimensional structural image of the eye and at least one biomechanical property of the eye. A feature extractor is configured to extract a plurality of features from the model of at least the cornea of the eye. An ectasia evaluation component is configured to calculate at least one parameter associated with the risk of ectasia in the eye from the extracted plurality of features. A system output is configured to provide the calculated at least one parameter to one of a treatment system and a user.

In accordance with another aspect of the present invention, a method is provided for evaluating ectasia risk in an eye. The eye is imaged at an imaging system to provide a three-dimensional structural image of the eye. A finite element model of at least the cornea of the eye is determined from the three-dimensional structural image of the eye and at least one biomechanical property of the eye. An input is received from a user adjusting at least one parameter of the model. The finite element model is reconciled to produce a predicted shape and biomechanical response of the eye given the adjustment. A plurality of features are extracted from the reconciled model. The patient is classified into one of a plurality of risk classes based upon the extracted plurality of features. At least one optical parameter is calculated from the predicted geometry.

In accordance with yet another aspect of the present invention, a method is provided for determining an optimal therapeutic intervention for an eye. The eye is imaged at an imaging system to provide a three-dimensional structural image of the eye. A finite element model of at least the cornea of the eye is determined from the three-dimensional structural image of the eye and at least one biomechanical property of the eye. An inverse finite element analysis is applied to the finite element model to determine an optimal set of therapeutic parameters for the therapeutic intervention. The optimal set of therapeutic parameters is provided to one of a user and a medical system associated with the therapeutic intervention.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

The invention includes systems and methods of utilizing computational model results for risk assessment and treatment guidance in the eye. Applications of the current invention include synthesizing and packaging finite element modeling results in the form of user-friendly surgical guidance and risk assessment tools that leverage the power of patient-specific computational modeling, while supplementing the modeling with probabilistic tools for clinical decision making.

In one implementation, the system can access ectasia risk in a therapeutic invention in the eye or optimize one or more parameters associated with such a procedure to minimize the ectasia risk. It will be appreciated that a "therapeutic procedure," can include any structure-altering ocular procedure. Examples include incision (e.g., astigmatic keratotomy, arcuate keratotomy, intrastromal incisions (such as Intracor and femtosecond astigmatic treatments), radial keratotomy, cataract incision, LASIK flap, and scleral incisions for presbyopia treatment), ablation (e.g., LASIK, PRK, Photo-therapeutic keratectomy), tissue extraction (e.g., femtosecond lenticule extraction with flap or small incision such as ReLEx and SMILE), collagen stiffening or weakening procedures, for example, with UV light and riboflavin, genapin, rose bengal, beta-nitroalcohols and other stiffening agents, for stabilization of the cornea, to address keratoconus and other forms of corneal instability or ectasia, stabilization of the sclera, to halt progression of axial myopia, reinforce sclera for mitigation of the stresses and strains that contribute to glaucomatous optic neuropathy, or alteration of shape of the sclera, cornea, or the crystalline lens for treatment of refractive error (e.g, photorefractive intrastromal crosslinking, scleral reinforcement or weakening for presbyopia treatment, lens shaping, or refractive index modification for refractive lens changes).

One implementation of the method provides an individualized biomechanical risk quantifier that estimates the likelihood of undercorrection, overcorrection or progressive shape distortion (ectasia) for a particular patient-specific model subjected to user-specified candidate treatments. The method could find application in refractive surgery screening clinics to account explicitly for patient-specific geometry and material properties that ultimately determine the structural response to procedures. In another implementation, a likelihood of a given optical/refractive outcome can be determined, and an appropriate optimization process can be employed for maximizing the likelihood of the desired outcome and minimizing the likelihood of structural instability and optical aberrations. Such determinations can be made for a specific patient or as part of a development effort to optimize a generalized approach in a virtual clinical trial that can be applied to individuals.

Figure 1:
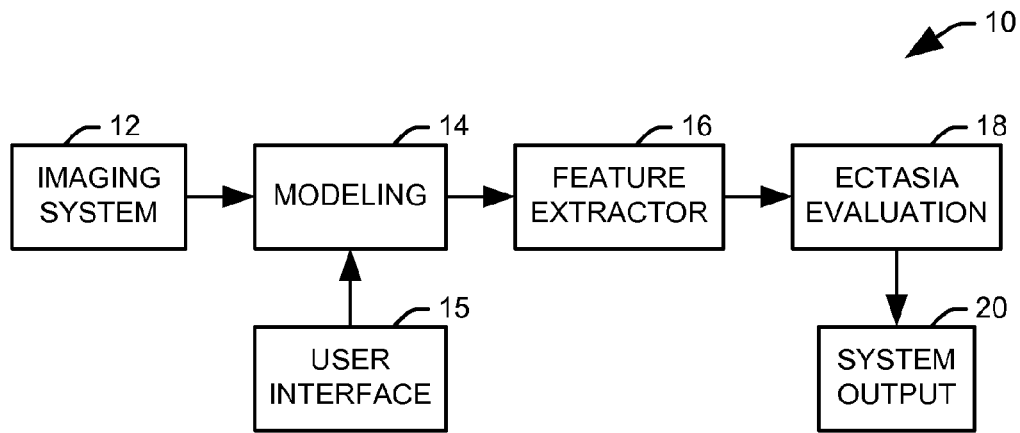
FIG. 1 illustrates a system for determining a risk of ectasia in a patient.

FIG. 1 illustrates a system 10 for determining a risk of ectasia in a patient. It will be appreciated that various elements of the illustrated system 10 can be implemented as computer programs, executable on one or more general purpose computers. Accordingly, any structures herein described can be implemented alternately as dedicated hardware circuitry for the described function or as a program code stored as part of a computer-assessable memory, such as a computer hard drive, random access memory, or a removable disk medium (e.g., magnetic storage media, flash media, CD and DVD media, etc.). Functions carried out by the illustrated system, but not helpful in understanding the claimed invention, are omitted from this diagram. For example, a system implemented as a computer program would require some amount of working memory and routines for accessing this memory. Such matters are understood by those skilled in the art, and they are omitted in the interest of brevity. It will be appreciated that, to the extent that components of the system 10 are implemented as software instructions, that they can be implemented on a single computer system or multiple, networked computer systems.

The system 10 comprises an imaging component 12 that is configured to provide a representation of a patient's eye. The imaging component 12 can utilize magnetic resonance imaging (MRI), optical coherence tomography (OCT), ultrasound, Scheimpflug imaging, Placido-based topography, multi-colored light emitting diode (LED) corneal shape analysis, scanning slit tomography, ultrasound biomicroscopy, arc-scanning ultrasound, or any other appropriate imaging modality or combination of modalities for establishing a three-dimensional geometry of at least the cornea. The determined images can be supplemented by additional values, such a determined axial length of the eye. It will be appreciated that, while the system 10, focuses on the cornea and the resulting visual effects, the representation of the patient's eye can further include, in one example, each of the sclera, the lens, the zonules, the choroid, the retina, the iris and, the ciliary body of the eye.

The images provided by the imaging component 12 can be digitized and processed as to obtain an overall geometry of the eye. For example, the images can be filtered and one or more edge detection algorithms can be utilized to determine the boundaries of the various tissue layers. Once the boundaries of the various tissue components is established, the processed image can be provided to a modeling component 14 configured to determine a representation of at least the cornea of the eye from the three-dimensional structural image and at least one biomechanical property of the eye. It will be appreciated that the biomechanical property of the eye can include, for example, Poisson's ratio, Young's modulus, or measures of elasticity or viscoelasticity, such as hysteresis, creep, stress relaxation, and a strain dependent function for Young's modulus, or poroelasticity, for each of the tissue types. It will be appreciated that these values can be provided according to a tissue type and age of the patient, for example, provided via a user interface 15 configured to allow the user to introduce one or more parameters of interest, such as the age, sex, medical history, and other medically relevant information concerning the patient. Alternatively, the biomechanical parameters can be specifically determined via an appropriate device, such as that described in U.S. Pat. No. 7,935,058, the contents of which are incorporated herein by reference. The elastography device described in this patent determines biomechanical properties of the cornea, including measures of elasticity or viscoelasticity, at each of a plurality of locations. Alternatively or additionally, the biomechanical parameters can be determined using manufacturer-provided output and custom variables derived from air-puff based commercial imaging tools such as the Reichert Ocular Response Analyzer and the Oculus CorvisST.

In one implementation, the modeling component 14 determines a three-dimensional finite element model of at least the cornea of the eye from the three-dimensional structural image and at least one biomechanical property of the eye. The finite element model represents a patient specific model of the eye that can be evaluated, either in its native form or with alterations representing proposed therapeutic procedures, to evaluate a risk of ectasia in the eye. In one implementation, the data from the imaging system 12 and the biomechanical property can be used at the modeling component 14 to generate a finite element model of the cornea, including displacements and strains on the corneal tissue from other portions of the eye. Alternatively, the biomechanical parameters can be provided as spatially varying functions of one or more parameters across a portion of the eye (e.g., the cornea and sclera), with the modeling component 14 utilizing the functions to model the biomechanical properties of the tissue. For example, the gradient of a measures of elasticity or viscoelasticity, such as hysteresis, stress relaxation, or creep can be determined in one or more directions, and a function describing the change in the elasticity or viscoelasticity can be derived (e.g., via a regression analysis) from the collected data.

In one implementation, the finite element model produced at the modeling component 14 can be implemented as a model of the cornea and sclera, with the forces exerted by the other tissue layers represented as an external force on the cornea tissue. Accordingly, while this reduced model does not directly incorporate extracorneal tissue into the model, known effects that have been characterized from the whole eye model can be incorporated into the model to maintain the influence of structures other than the cornea and sclera on the corneal shape. It will be appreciated that the force representing the effects of the extracorneal structures can be determined according to specific characteristics of a patient's eye, including known geometric properties derived from the image data as well as any measured or estimated values for biomechanical properties of the extracorneal tissue.

In another implementation, the modeling component 14 determines the representation of at least the cornea of the eye as virtual model comprising a set of parameters extracted from evaluating a statistical model according to the three-dimensional structural image and at least one biomechanical property of the eye. Specifically, the three-dimensional structural image of the eye and other modeling variables, such as corneal material properties, when available, or an age surrogate, or a surgical treatment plan can be input to a generalized model generated from a multivariate statistical model fit to the results of the prior parametric studies within a reference library. The output of this generalized model is a set of modeling response variables that would ordinarily be extracted from a finite element model. This is computationally much more efficient and can be achieved, for example, through multivariate linear or nonlinear regression, Kriging regression, and other 'surface response' models.

A feature extractor 16 extracts feature data comprising a plurality of features from the provided model. In one example, the feature extractor 16 extracts feature values from the generated model according to a set of selected features. The selected features can be any values derived from the model that are useful in predicting or optimizing one or more parameters of interest in assessing and mitigating ectasia risk. Numerical data extracted from the features can be conceived for computational purposes as a feature vector, with each element of the vector representing a value derived from one feature within the model. Specific features can be selected by any reasonable method, but typically, appropriate features will be selected by experimentation and prior success.

In one implementation, the feature extractor 16 can extract measurements from the determined model, such as the thicknesses of various tissue layers within the eye, as well as calculated values, such as Zernike polynomials for the cornea and optical power values (e.g., apical and tangential values). Further, the feature extractor 16 can calculate one or more measures of elasticity or viscoelasticity for the cornea at one or more locations from the model. The measures can include hysteresis, creep, stress relaxation, and a strain dependent function for Young's modulus for any of a plurality of locations of interest within the eye, particularly the cornea and sclera.

Further examples of corneal features extracted from the model can include a spatial variation of corneal elasticity, measured, for example, as a parametric or nonparametric measure of variation (e.g., standard deviation) among a plurality of measured locations or as a gradient mapping of the cornea in one or more dimensions. Similarly, where the patient has already undergone a surgical or nonsurgical intervention, a difference in elasticity between sections subjected to collagen cross-linking or abnormal strains near the flap region after refractive procedure can be determined. Differences in biomechanical properties, including viscoelasticity and elasticity measures, from normal corneal tissue can also be determined for regions of residual stroma bed after a refractive surgery procedure. In addition, native heterogeneity within cornea is of interest during screening of patients, which can be measured, for example, as a measure of variation of one or more elasticity parameters or as a set of gradients determined from the measured values. For example, a maximum gradient or an average of a set of highest gradients can be utilized as a feature.

Additional features can include features representing various regions of the cornea and sclera. For example, features representing elasticity measures and gradients from various regions of the cornea, for example, the anterior portion or posterior portion of the cornea, as well as derived values (e.g., ratios and differences) intended to compare the properties of the two regions. Similar measures can be determined for a central portion of the cornea and a peripheral portion, and any other locations of interest for a given therapeutic procedure. Such regional features are of particular interest in detecting the onset of keratoconus, a known risk factor for refractive surgery, as regional and local abnormalities around stress/strain peaks can be detected. Accordingly, any of these derived parameters from the elasticity data can be utilized as part of the feature vector, depending on the parameters of interest for the system 10.

In one implementation, the feature extractor 16 can extract features from a finite element model that has been altered to represent a load on the eye, such as an increase in intraocular pressure (IOP) or one or more structural or material changes to the eye. For example, an appropriate alteration can be entered via the user interface 15 to represent material or structural changes to the eye from a therapeutic procedure, for example, having a plurality of therapeutic variables derived from a planned therapeutic intervention. The features can then be selected to evaluate the success of the procedure and the risk of ectasia in the aftermath of the procedure.

Alternatively, the alteration can simulate a load on the current state of the eye tissue to extract features associated with an inherent risk of ectasia in the patient. Extracted features can include one or more optical parameters, such as optical power values (e.g., tangential and axial diopters), Zernike polynomials, or simulated keratometry ($K_{max}$) values characterizing the shape of the cornea, stress and strain values (e.g., principle stress and strain components, superior-inferior stress and strain components, Mises stress, etc.) in the altered model at various locations, maximum stress and strain values, and displacements in the tissue before and after the alterations. The inventor has determined that higher stress and strain values as well as non-uniform and asymmetric distributions of biomechanical properties across the eye correlate well with ectasia risk, and appropriate features can be extracted can be selected to exploit this correlation. Similarly, the inventor has determined that a simulated increase in IOP tends to result in different trends in $K_{max}$ in eyes with or at risk for ectasia than in normal eyes.

In one example, in accordance with an aspect of the present invention, the determined model can be corrected for intraocular pressure (IOP) such that the changes applied to simulate a therapeutic procedure are applied to an "inverse model" that is adjusted to reflect the condition of the patient's eye absent intraocular pressure. Once the changes have been applied, the reconciled model can be adjusted to include an appropriate value for the patient for intraocular pressure. It will be appreciated that the influence of intraocular pressure on the corneal shape can be significant, and has been determined, through use of a whole eye model in accordance with an aspect of the present invention, to depend greatly on the material properties of the cornea. Accordingly, the results of a therapeutic intervention, particularly refractive surgery, can vary significantly according to the stiffness of the corneal tissue and the intraocular pressure of the eye.

In one implementation, the feature extractor 16 can generate a plurality of instances of the model, reflecting different variables for a therapeutic procedure, and extract the features from the model instances. Specifically, one or more features representing the optical properties and stability of the eye after a simulated procedure or the application of a load on the eye can be extracted and paired with the input variables to provide sets of input and output data for an optimization process. Alternatively, the feature extractor 16 can extract features from the model representing the structure and biomechanical properties of the eye. These values can be utilized by an optimization process, such as an analogical reasoning algorithm, to locate therapies that have been successful in similar eyes.

The extracted feature vector can be provided to an ectasia evaluation component 18 configured to calculate at least one parameter associated with the risk of ectasia in the eye from the extracted plurality of features. It will be appreciated that the at least one parameter can be a prediction of the rick of ectasia in the eye or a variable associated with a therapeutic intervention to reduce the risk of ectasia associated with a procedure. In one implementation, the ectasia evaluation component 18 can include a regression model configured to provide calculate a parameter representing an expected risk of ectasia to the patient given a therapeutic procedure having the associated type and location. In yet another implementation, the ectasia evaluation component 18 can perform a sensitivity analysis using the model, such that a magnitude of the effect of one or features on the at least one parameter can be determined.

In another implementation, the ectasia evaluation component 18 comprises a classification algorithm configured to select a risk class for the patient's eye from the extracted features. Any of a variety of optimization techniques can be utilized for the classification algorithm, including support vector machines, self-organized maps, fuzzy logic systems, data fusion processes, ensemble methods, rule based systems, or artificial neural networks. Each outcome class represents a predicted range of outcomes for the patient given the application of the therapeutic procedure. This can range from a binary "good" and "bad" to a plurality of graduations of ectasia risk. Ideally, the training data represents feature vectors and associated outcomes for previous patients, although data from a whole-eye model could be utilized initially in training and testing the classifier model. From the provided feature vector, an outcome class is selected and a confidence in the selected result can be calculated. Results falling below a threshold confidence value can be rejected.

In another set of implementations, the ectasia evaluation component 18 is configured to select optimal parameters for a therapeutic procedure from the extracted features. In one example, the ectasia evaluation component 18, in combination with the feature extractor 16, to perform an inverse finite element modeling analysis on the modeled eye according to a provided objective function. In another example, the ectasia evaluation component 18 can be implemented as an analogical reasoning algorithm to locate therapies that have been successful for patients having eyes with similar properties to the modeled eye. In yet another example, a finite element model can be used with a genetic algorithm to generate an optimal set of therapeutic variables for a therapeutic procedure. This optimal set of parameters can include one or more of a geometric characteristic of an incision, a geometric characteristic of an ablation, and a geometric or material property of a crosslinking treatment.

In practice, model results, whether obtained as one or more forward models of a procedure or an inverse optimization with a recommended treatment plan, can be evaluated not only for the eye of interest but also for a group of model eyes with similar or slightly varied geometrical and biomechanical characteristics. In one implementation, the ectasia evaluation component can classify the patient into a class containing similar patients using the extracted features. In another implementation, a set of models similar to the modeled eye can be selected via an analogical reasoning algorithm.

The ectasia evaluation component 18 can be generate probabilities of a desired outcome or likelihoods of ectasia based on multiple model runs in the virtual patient panel for the selected patient class, with measures of variance provided as an estimate of possible prediction error. The size of a virtual patient modeling run can vary depending on the number of appropriate patients available within the reference library, and additional virtual patients can be generated by changing geometric or biomechanical characteristics slightly. For example, a set of parameters that can be changed to generate the variance in the reference dataset needed for a robust model include the reference eyes themselves as represented by their 3-D geometry as derived by the imaging system 12 or a similar imaging device, a range of surgical parameters, such as the location and dimensions of surgical cuts/ablations/crosslinking exposure patterns/depths, that are germane to a specific surgery type (LASIK, PRK, crosslinking, and a range of eye material property assumptions to account for sensitivity to this assumption or errors in its actual measurement.

Further, a design-of-experiments type analysis can be employed to determine the sensitivity of an outcome to certain surgical or treatment variables or patient risk characteristics, such as the shape and material properties of the eye. The sensitivity information can be derived from a number of sample eyes, and collectively reduced to a general model, for example, in a software application, that allows a user to toggle individual parameters and observe the change in expected outcome.

One parameter of particular interest in sensitivity analysis the effect of decreasing corneal elastic strength on the model variables for the eye of a given patient. If the value for elastic strength is varied in the model across a range centered on the expected corneal property for that eye, a slope for geometric/optical/mechanical change is for that eye. This allows a clinical to assess more delicate cases that appear to be highly sensitive to material assumptions. In other words, if the outcome is not that variable across a range of corneal strength assumptions and the slope is low, that eye is less sensitive to variations in an intended end state than an eye that is highly sensitive. Accordingly, varying the material assumption allows for an accurate assessment of risk. The sensitivity analysis also aids in generation confidence intervals around optimizations of therapeutic techniques, as is discussed in detail in FIG. 4, below.

Once the at least one parameter has been determined at the ectasia evaluation component 18, the parameter(s) are provided to a system output 20 configured to provide the calculated at least one parameter to one of a treatment system and a user. The system 10 can be configured to allow empirical modification of model-based outcome predictions and optimal treatment plans using previously collected aggregate or user-specific clinical outcomes from similar cases. The user interface 15 and the output component 20 can be configured to allow users to separately view or interact with patient-specific model-driven predictions or treatment optimizations or optimized treatments from a structurally similar virtual patient group predictions, and the empirically modified treatment plan.

In one example, a user may wish to reduce a patient's astigmatism and plans a particular pattern, orientation and intensity distribution of ultraviolet (UV) light to generate a pattern of corneal stiffening that might reduce the astigmatism. The system 10 can be employed in a number of ways to reduce the risk of ectasia and improved overall outcome in this treatment. For example, the system 10 can be used to model the patient's eye and calculate a forward simulation of the proposed treatment with a comparison to a desired outcome, calculate two or more forward simulations exploring variations in parameters, or an automated optimization solving for treatment parameters most likely to produce the desired change in astigmatism. Similarly, one or both of forward simulation and inverse optimization can be employed, with the results for the specified patients are compared to similar modeling simulations in a virtual patient database to generate a range of potential outcomes and desirable treatment parameters. The user interface 15 can allow access to an interactive application that allows user-driven modification of treatment parameters and recall of modeling results based on full model runs or reduced algorithms representing the relationships between simulated variables. If a database of prior outcomes is available, the system 10 allows for plan modification based on an error minimizing algorithm or other optimization algorithm. The system 10 can be accessed as a freestanding software package, a web-based application, a mobile application, or as a feature built into a surgical system, in this example, the UV delivery system. Treatment planning can be manual, interactive, or automated with a direct link between the invention and the code that controls UV intensity, duration, pattern, and orientation.

In the case of crosslinking, physical principles can be used to determine the treatment parameters required to achieve the desired stiffening effect determined by the model and in the geometric distribution determined by the model. Such relationships might incorporate the Fick diffusion law to estimate the duration of exposure required to deliver the necessary amount of riboflavin or other agent to the treatment regions, the Lambert-Beer law or other descriptions of light absorption to estimate the amount of photons available for reaction, oxygen diffusion relationships and reaction kinetics relationships to estimate the amount of photoactivation occuring, and correlations between these variables and actual stiffness measurements in tissue. Clinical results of the treatment at a determined stability endpoint would be collected and incorporated into the treatment library for empirical comparisons and model refinement, and the patient model would be added to the virtual patient library.

Figure 2:
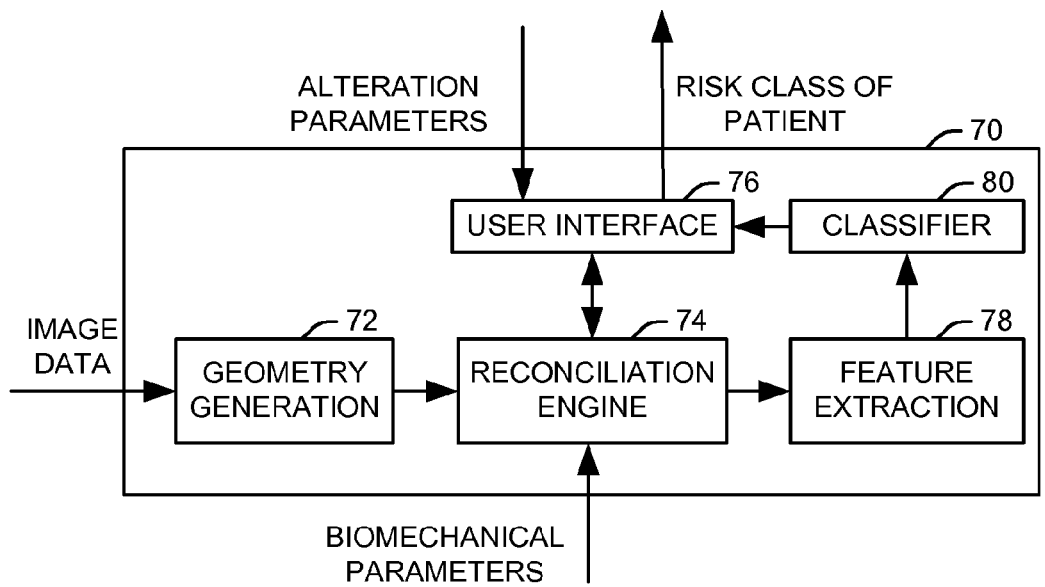
FIG. 2 illustrates a functional block diagram of one example of a finite element analysis (FEA) predictive modeler.

FIG. 2 illustrates a functional block diagram of one example of a finite element analysis (FEA) predictive modeler 70, stored on as computer executable instructions on computer readable medium, that is executable to predict the results of a therapeutic intervention on a patient's eye according to a finite element analysis (FEA) of the eye. Each functional block illustrated in the diagram represents a series of executable instructions stored in the computer readable medium configured to perform the described function. It will be appreciated, however, that the various functional blocks can be configured to utilize functional instructions from an associated operating system or other common library sources in executing their associated functions. The illustrated FEA predictive modeler 70 receives data representing the eye of a given patient and constructs a model based on this data. A user can select a customized therapeutic intervention for the eye, represented as a series of therapeutic parameters. From the constructed model and the therapeutic parameters, a predicted shape of the eye, given the therapeutic intervention, can be determined. The predicted shape and at least one optical parameter calculated from the shape can be provided to the user at an associated display to illustrate the predicted surgical outcome to the user.

The FEA predictive modeler 70 receives image data representing the patient's eye at a geometry generation element 72. It will be appreciated that the image data can be provided directly from an imaging system or provided to the predictive modeler 70 as data stored on a computer readable medium. The geometry generation element 72 forms a three-dimensional representation of the patient's eye from the image data. For example, a two-dimensional image can be rotated to form a three-dimensional representation of the eye. The thicknesses of the various tissue layers can be provided as parameters from an associated database (not shown). Where the imaging modality allows for a three-dimensional image of the eye, the geometry can be determined directly from the image.

Once the boundaries of the various tissue components is established, the processed image data can be provided to a reconciliation engine 74 that establishes a finite element model of the ocular tissue according to the determined geometry of the eye and one or more biomechanical parameters for each of the tissue types. For example, the biomechanical parameters for the cornea can include parameters, such as Poisson's ratio, Young's modulus, or measures of viscoelasticity or elasticity, such as hysteresis, creep, stress relaxation, and a strain dependent function for Young's modulus, or poroelasticity, for each of the corneal tissue generally and for flap wounds in the cornea. These values can be taken from known average values for the appropriate tissue types or determined directly from the patient for one or more tissue types via measurement of the tissue properties under stress. It will be appreciated, however, in accordance with an aspect of the present invention, that where spatial variance of the biomechanical properties of the tissue from the average can be ascertained, individualized values can be used for the various finite element values within a given tissue type.

Once the geometry and biomechanical properties for the various finite elements comprising the model have been established, selected elements can be altered by a user at a user interface 76 to represent a therapeutic intervention or a load applied to the eye. For example, a user can alter one or both of the thickness or biomechanical properties of the model for a given region of tissue as to simulate a therapeutic procedure, such as LASIK flaps or regions of cornea exposed to a collagen cross-linking agent. In accordance with an aspect of the present invention, a set of standard therapeutic patterns can be provided as part of a pattern database (not shown) for application to the model, providing a user with a series of standard treatments as well as appropriate starting points for the user to design a custom treatment for the modeled eye.

The model, including the alterations, can be solved at the reconciliation engine 74 to provide a predicted geometry of the eye given the therapeutic intervention. Once the predicted geometry has been determined, it can be displayed to the user at the user interface 76. Further, one or more parameters associated with the shape of the cornea in the determined geometry can be provided to a feature extractor 78. The feature extractor 78 calculates one or more properties of the eye. In one example, the features include one or more optical power values and a series of Zernike polynomials. For example, the apical power, $F_a$, is given by:

$$F_a = \frac{n_c - 1}{R_a} \quad \text{Eq. 1}$$

where $R_a$ is the apical radius of curvature.

To analyze the tangential power, the anterior surface can be approximated as a conic equation about the z-axis (the elevation axis) and radius, r,—such as:

$$r = \sqrt{2R_a + z^2 - (ez)^2} \quad \text{Eq. 2}$$

where e is the eccentricity and $R_a$ is the apical radius of curvature.

The local radius of curvature can therefore be computed as:

$$R = \sqrt{R_a^2 + (ez)^2} \quad \text{Eq. 3}$$

The tangential power, F, can be determined from this value as:

$$F = \frac{n_c - 1}{R} \quad \text{Eq. 4}$$

where $n_c$ is the refractive index of the cornea.

It will be appreciated that, given the alteration to the model, the extracted features can represent changes (e.g., relative expression of post-alteration model features minus the corresponding pre-alteration model features) or in absolute terms derived using input such as axial eye length, patient refractive error from clinical refraction or thick lens optical calculations or ray tracing through ocular surfaces, whole-eye or corneal aberrations from clincal aberrometry, or data such as global and local corneal stresses and strains.

The extracted feature vector is then provided to a pattern recognition classifier 80. At the classifier, the feature vector, representing the patient's data, is, via an appropriate optimization algorithm, compared to training data representing each of a plurality of risk classes. Any of a variety of optimization techniques can be utilized at the pattern recognition classifier for making this determination, including support vector machines, self-organized maps, fuzzy logic systems, data fusion processes, expert systems, rule, case based systems, or algorithmic programs, or any of a variety of neural network classifiers. Each risk class represents a predicted range of outcomes for the patient. Ideally, the training data represents feature vectors and associated outcomes for previous patients, although data from a whole-eye model could be utilized initially in training and testing the classifier model. From the provided feature vector, a risk outcome class is selected and provided to the user via the user interface 76. In one implementation, the selected class can be displayed to the user in a graphical user interface (GUI) along with customary clinical corneal and refractive metrics such as refractive error, corneal surface, curvatures (including axial/sagittal and tangential/instantaneous curvature representations), corneal surface elevations, and corneal aberrations (using Zernike polynomial expressions, including lower order aberrations and higher order aberrations such as spherical aberration and coma, for example).

Figure 3:
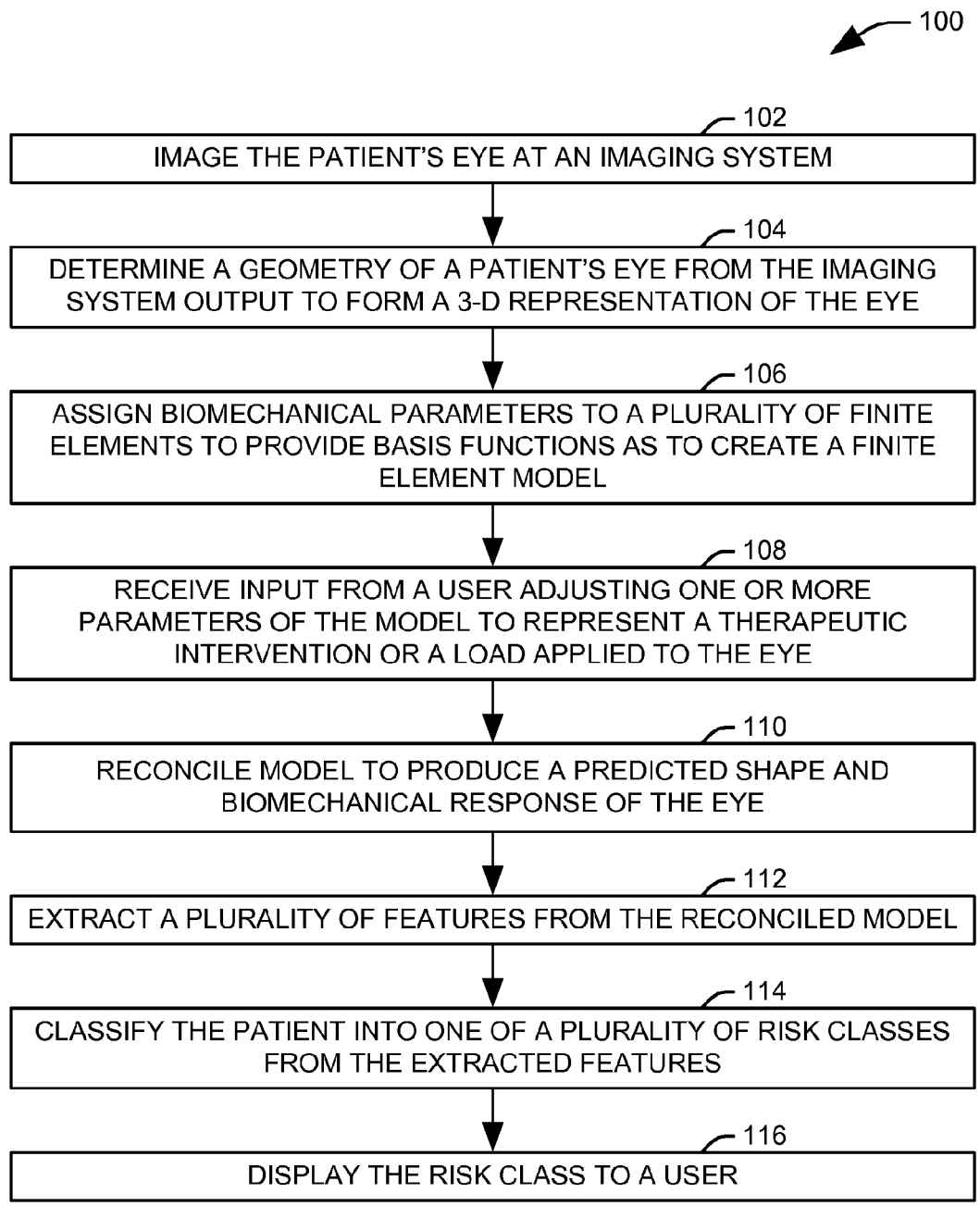
FIG. 3 illustrates a method for predicting the outcome of a surgical outcome.
Figure 4:
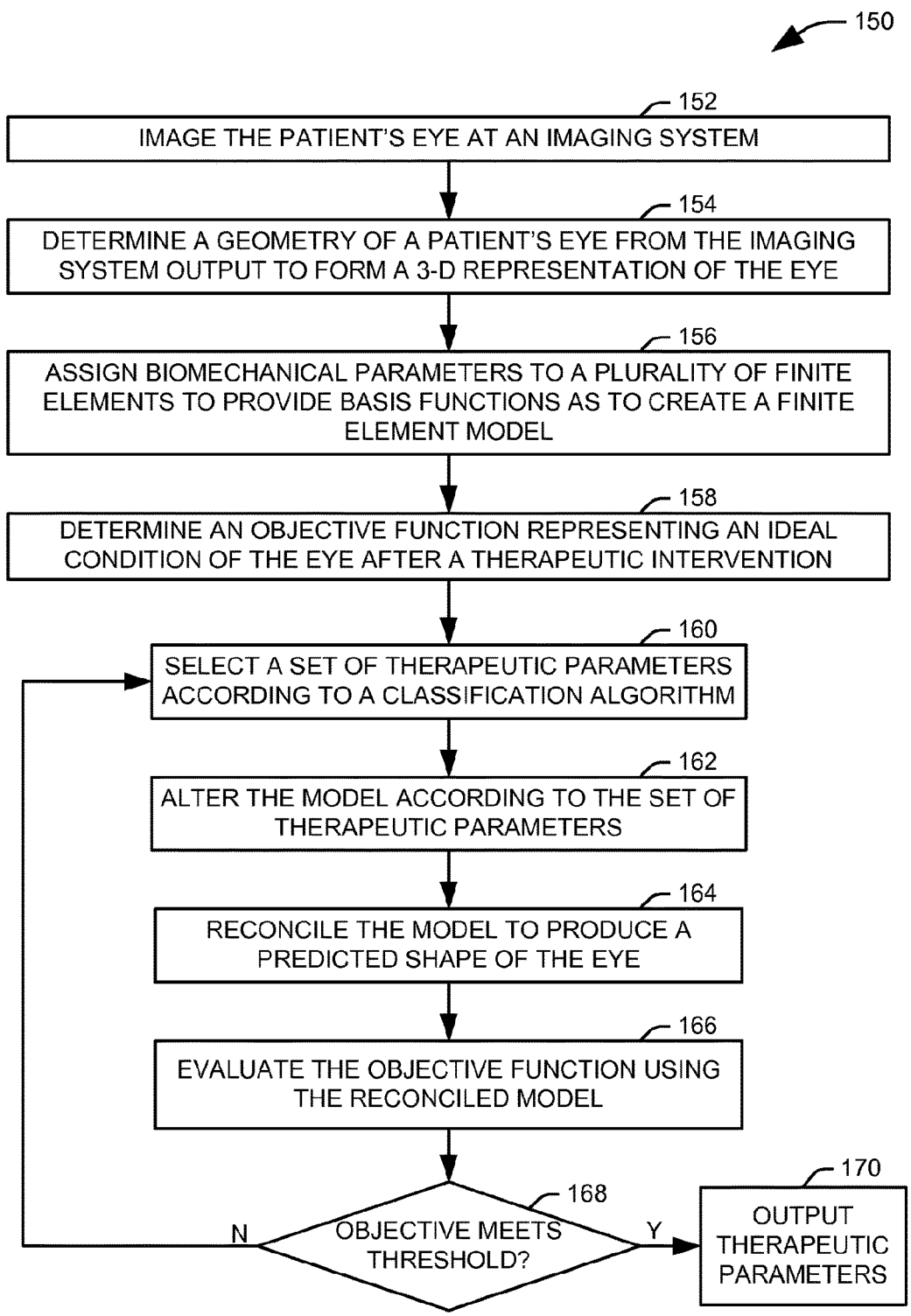
FIG. 4 illustrates a method for determining optimal variables for a therapeutic intervention.

In view of the foregoing structural and functional features described above, methods in accordance with various aspects of the present invention will be better appreciated with reference to FIGS. 3 and 4. While, for purposes of simplicity of explanation, the methods of FIGS. 3 and 4 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 3 illustrates a method 100 for predicting the outcome of a surgical outcome. The methodology begins at 102, where an eye of a patient is imaged by an imaging system. For example, the imaging system can include a magnetic resonance imaging system (MRI), a computer tomography (CT) system, or any other appropriate image system for determining a three-dimensional geometry of the eye. At 104, the generated image is used to construct a three-dimensional representation of the geometry of the patient's eye. For example, a two-dimensional image can be axially rotated to provide a representation of the patient's eye. Standard thickness values for various tissue layers can used to simulate a three-dimensional model. Where a three-dimensional imaging of the whole eye has been performed, the geometry of the patient's eye can be derived directly from the imaging data. In one implementation, the image is obtained from an anterior segment imaging device, and example image sources can include Scheimpflug tomography, optical coherence tomography (OCT), multi-colored LED corneal shape analysis, Placido-based topography, scanning slit tomography, ultrasound biomicroscopy, and arc-scanning ultrasound.

At 106, the three-dimensional representation is divided into a plurality of finite elements, each represented by an associated function. Biomechanical parameters of the eye tissue are assigned to the associated functions of the plurality of finite elements to provide a finite element model of the eye. The associated functions reflect the behavior of a given portion of the tissue under stress and strain from other portions of the eye and intraocular pressure. The biomechanical parameters representing the eye tissue can be determined via direct measurement or known representative results for each tissue, for example, according to an age and/or disease cohort of the patient, can be utilized.

At 108, a user provides an alteration to the model that simulates either loading or the effects of a therapeutic procedure. For example, an appropriate pattern of changes to the geometry and biomechanical properties of the model can be selected at a graphical user interface to simulate one of a variety of refractive surgical procedures, an application of a collagen cross-linking treatment, or some form or loading or stress applied to the eye, such as an increase in intraoperative pressure. In one implementation, the patterns can be customizable, allowing a user to input a customized therapeutic procedure to produce optimal results.

At 110, the finite element model is reconciled to incorporate the changes provided by the user to provide a predicted shape of the eye. A plurality of features can be extracted from the reconciled model at 112. The extracted features can include optical parameters, stress and strain values (e.g., principle stress and strain components, superior-inferior stress and strain components, Mises stress, etc.) in the altered model at various locations, maximum stress and strain values, and differences in these values between the original model and the altered model. At 114, the user is sorted into a risk class, representing the risk of ectasia to the patient, using an appropriate classification algorithm, and the selected class is displayed to a user at 116.

FIG. 4 illustrates a method 150 for determining optimal variables for a therapeutic intervention. The variables in the optimizations can include any surgical parameter that can be varied by a clinician in a therapeutic intervention, for example, the length, depth or other geometric characteristic of an incision or group of incisions, the depth, diameter, profile, or other geometric characteristic of an ablation (as in LASIK or PRK, for example), or the pattern, depth, stiffness profile or other geometric and material property characteristics of a crosslinking treatment to selectively stiffen the cornea for a desired refractive outcome. Multiple parameters can be optimized, including stress and strain distributions, to minimize the undesired biomechanical impact of certain procedures and maximize the desired optical outcome simultaneously.

The methodology begins at 152, where an eye of a patient is imaged by an imaging system. For example, the imaging system can include a magnetic resonance imaging system (MRI), a computer tomography (CT) system, or any other appropriate image system for determining a three-dimensional geometry of the eye. At 154, the generated image is used to construct a three-dimensional representation of the geometry of the patient's eye. For example, a two-dimensional image can be axially rotated to provide a representation of the patient's eye. Standard thickness values for various tissue layers can used to simulate a three-dimensional model. Where a three-dimensional imaging of the whole eye has been performed, the geometry of the patient's eye can be derived directly from the imaging data. In one implementation, the image is obtained from an anterior segment imaging device, and example image sources can include Scheimpflug tomography, optical coherence tomography (OCT), multi-colored LED corneal shape analysis, Placido-based topography, scanning slit tomography, ultrasound biomicroscopy, and arc-scanning ultrasound.

At 156, the three-dimensional representation is divided into a plurality of finite elements, each represented by an associated function. Biomechanical parameters of the eye tissue are assigned to the associated functions of the plurality of finite elements to provide a finite element model of the eye. The associated functions reflect the behavior of a given portion of the tissue under stress and strain from other portions of the eye and intraocular pressure. The biomechanical parameters representing the eye tissue can be determined via direct measurement or known representative results for each tissue, for example, according to an age and/or disease cohort of the patient, can be utilized. It will be appreciated that, in lieu of the full finite element model, a reduced model can be selected to more efficiently capture the behavior of the eye in response to therapeutic changes can be employed. For example, one or more portions of the eye could be absent from the reduced finite element model but modeled as influences on the cornea.

At 158, an objective function is determined, representing an ideal end state of the eye after the therapeutic intervention. End-user outcome metrics such as refractive outcome can be defined using clinical manifest refraction, autorefractometry, or wavefront aberrometry, and a model refractive outcome can be derived from the metrics. Further, to account for a risk of post-therapeutic ectasia, other factors can be included in the objective function, such as stress and strain values (e.g., principle stress and strain components, superior-inferior stress and strain components, Mises stress, etc.) in the altered model at various locations, maximum stress and strain values, differences between the stress and strain values before and after application of a simulated therapeutic intervention, and displacements in the tissue before and after the simulated therapeutic intervention At 160, a set of therapeutic parameters, defining a proposed therapeutic intervention, is selected. In one implementation, a default or user provided set of parameters can be selected initially, with subsequent sets selected according to an optimization routine to most efficiently optimize the objective function. Any appropriate optimization function can be used to select the parameters. At 162, an alteration to is made to the model to simulate the defined therapeutic procedure. For example, an appropriate pattern of changes to the geometry and biomechanical properties of the model can be selected at a graphical user interface to simulate one of a variety of refractive surgical procedures, an application of a collagen cross-linking treatment. At step 164, the finite element model is reconciled to incorporate the changes provided by the user to provide a predicted shape and biomechanical response of the eye.

At 166, the objective model is evaluated using feature values extracted from the reconciled function to produce an objective value. At 168, it is determined if the objective value meets a threshold. It will be appreciated that, depending on the format of the objective function, it may be desirable to produce a minimum or maximum value of the function, and the threshold can be selected accordingly. If the objective value does not meet the threshold (N), the method returns to 160 to select a new set of therapeutic parameters. When the objective function meets the threshold (Y), the therapeutic parameters are provided to either a user, for example, via a display, or a medical system associated with the procedure at 170. The result of the method is a surgical plan that can be presented to a user and compared to a preliminary plan that can be adjusted manually by the user or, in another implementation, directly incorporated into a treatment algorithm as an add-on or built-in function of an eye surgery device, such as an excimer laser, a femtosecond laser, a UV light delivery source, or chemical crosslinking delivery system employing iontophoresis.

Figure 5:
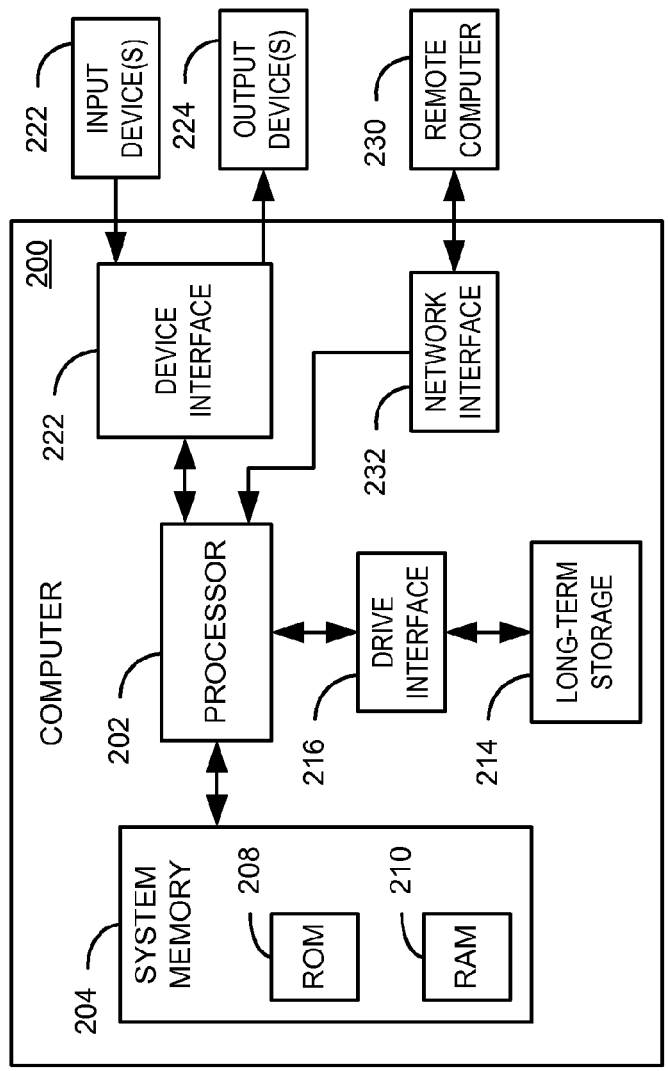
FIG. 5 illustrates a computer system that can be employed to implement systems and methods described herein, such as based on computer executable instructions running on the computer system.

FIG. 5 illustrates a computer system 200 that can be employed to implement systems and methods described herein, such as based on computer executable instructions running on the computer system. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. Dual microprocessors and other multi-processor architectures can also be utilized as the processor 202. The processor 202 and system memory 204 can be coupled by any of several types of bus structures, including a memory bus or memory controller, a peripheral bus, and a local bus using any of a variety of bus architectures. The system memory 204 includes read only memory (ROM) 208 and random access memory (RAM) 210. A basic input/output system (BIOS) can reside in the ROM 208, generally containing the basic routines that help to transfer information between elements within the computer system 200, such as a reset or power-up.

The computer system 200 can include one or more types of long-term data storage 214, including a hard disk drive, a magnetic disk drive, (e.g., to read from or write to a removable disk), and an optical disk drive, (e.g., for reading a CD-ROM or DVD disk or to read from or write to other optical media). The long-term data storage can be connected to the processor 202 by a drive interface 216. The long-term storage components 214 provide nonvolatile storage of data, data structures, and computer-executable instructions for the computer system 200. A number of program modules may also be stored in one or more of the drives as well as in the RAM 210, including an operating system, one or more application programs, other program modules, and program data.

A user may enter commands and information into the computer system 200 through one or more input devices 220, such as a keyboard or a pointing device (e.g., a mouse). These and other input devices are often connected to the processor 202 through a device interface 222. For example, the input devices can be connected to the system bus by one or several parallel ports, a serial port or a universal serial bus (USB). One or more output device(s) 224, such as a visual display device or printer, can also be connected to the processor 202 via the device interface 222.

The computer system 200 may operate in a networked environment using logical connections (e.g., a local area network (LAN) or wide area network (WAN) to one or more remote computers 230. A given remote computer 230 may be a workstation, a computer system, a router, a peer device or other common network node, and typically includes many or all of the elements described relative to the computer system 200. The computer system 200 can communicate with the remote computers 230 via a network interface 232, such as a wired or wireless network interface card or modem. In a networked environment, application programs and program data depicted relative to the computer system 200, or portions thereof, may be stored in memory associated with the remote computers 230.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, the following is claimed:

1. A system for evaluating an eye of a patient, comprising:
   a modeling component configured to determine a representation of at least the cornea of the eye from a three-dimensional structural image of the eye and at least one biomechanical property of the eye;
   a feature extractor configured to extract a plurality of features from the model of at least the cornea of the eye;
   a user interface configured to accept input from a clinician defining an objective function as a function of at least one parameter for the eye after the therapeutic procedure;
   an ectasia evaluation component configured to calculate at least one parameter associated with the risk of ectasia in the eye from the extracted plurality of features and the objective function, the calculated at least one parameter including a variable in a therapeutic procedure representing a surgical parameter that can be varied by a clinician in the therapeutic procedure; and
   a system output configured to provide the calculated at least one parameter to one of a treatment system and a user.

2. The system of claim 1, the modeling component being configured to determine a three-dimensional finite element model of at least the cornea of the eye from the three-dimensional structural image and at least one biomechanical property of the eye.

3. The system of claim 2, wherein the modeling component is configured to provide a three-dimensional finite element model representing the eye after the therapeutic procedure, the system further comprising a user interface configured to accept input from a clinician defining at least a type and location of the therapeutic procedure.

4. The system of claim 3, wherein the feature extractor is configured to extract the at least one feature of the plurality of features from the three-dimensional finite element model representing the eye after the therapeutic procedure, the ectasia evaluation component being configured to calculate a parameter representing an expected risk of ectasia to the patient given a therapeutic procedure having the associated type and location.

5. The system of claim 4, the ectasia evaluation component being configured to perform a sensitivity analysis on at least one feature, such that a magnitude of an impact of the value of the at least one feature on the at least one parameter can be determined.

6. The system of claim 4, wherein the extracted at least one feature represents one of a geometric or biomechanical characteristic of the eye.

7. The system of claim 2, wherein the modeling component is configured to provide a three-dimensional finite element model representing the eye with a load applied to the eye, the system further comprising a user interface configured to accept input from a clinician defining at least a magnitude and location of the load.

8. The system of claim 1, the modeling component being configured to determine an finite element model of at least the cornea of the eye from the three-dimensional structural image and at least one biomechanical property of the eye.

9. The system of claim 8, wherein the ectasia evaluation component comprises an optimization algorithm and the feature extractor and the ectasia evaluation component are configured to, in combination with the determined finite element model, perform an inverse finite element modeling analysis on the eye to provide the variable in the therapeutic procedure.

10. The system of claim 9, the variable in the therapeutic procedure comprising one of a geometric characteristic of an incision, a geometric characteristic of an ablation, and a geometric or material property of a crosslinking treatment.

11. The system of claim 1, wherein the objective function is a function of at least one of a strain value of the eye and a stress value of the eye.

12. The system of claim 1, wherein the objective function is a function of at least one measure of refractive outcome.

13. The system of claim 1, wherein the modeling component determines the representation of at least the cornea of the eye as a virtual model comprising a set of parameters extracted from evaluating a statistical model according to the three-dimensional structural image and at least one biomechanical property of the eye.

14. The system of claim 13, wherein the ectasia evaluation component comprises an optimization algorithm and the feature extractor and the ectasia evaluation component are configured to, in combination with the determined virtual model, perform an inverse finite element modeling analysis on the eye to provide the variable in the therapeutic procedure.

15. The system of claim 13, wherein the modeling component is configured to provide a virtual model representing the eye after a therapeutic procedure, the system further comprising a user interface configured to accept input from a clinician defining at least a type and location of the therapeutic procedure.

\* \* \* \* \*